United States Patent
Minkara et al.

(10) Patent No.: US 9,651,497 B2
(45) Date of Patent: May 16, 2017

(54) METHOD AND DEVICE TO DETERMINE ADSORPTION CAPACITY FOR AIR ENTRAINING AGENTS

(71) Applicant: Headwaters Incorporated, South Jordan, UT (US)

(72) Inventors: Rafic Y. Minkara, Kennesaw, GA (US); Jennifer M. Kelley, Taylorsville, GA (US); Crystal A. Dixon, Fenton, MO (US); Richard J. Nordman, Fenton, MO (US); Michael J. Ponstingl, Fenton, MO (US)

(73) Assignee: Headwaters Incorporated, South Jordan, UT (US)

( * ) Notice: Subject to any disclaimer, the term of this patent is extended or adjusted under 35 U.S.C. 154(b) by 0 days.

(21) Appl. No.: 15/027,537

(22) PCT Filed: Oct. 10, 2014

(86) PCT No.: PCT/US2014/060001
§ 371 (c)(1),
(2) Date: Apr. 6, 2016

(87) PCT Pub. No.: WO2015/054556
PCT Pub. Date: Apr. 16, 2015

(65) Prior Publication Data
US 2016/0238537 A1 Aug. 18, 2016

Related U.S. Application Data

(60) Provisional application No. 61/889,749, filed on Oct. 11, 2013.

(51) Int. Cl.
*G01N 21/77* (2006.01)
*G04B 18/08* (2006.01)
(Continued)

(52) U.S. Cl.
CPC ............ *G01N 21/77* (2013.01); *C04B 18/08* (2013.01); *C04B 28/02* (2013.01);
(Continued)

(58) Field of Classification Search
CPC ..... C04B 18/08; C04B 28/02; C04B 40/0039; C04B 20/023; C04B 2103/304;
(Continued)

(56) References Cited

U.S. PATENT DOCUMENTS 5,596,146 A 1/1997 Waller et al.
6,136,089 A * 10/2000 Hurt .................... C04B 18/08
106/405

(Continued)

FOREIGN PATENT DOCUMENTS

JP 2005180726 A 7/2005

OTHER PUBLICATIONS

International Search Report and Written Opinion mailed Jan. 23, 2015 for PCT/US2014/060001 filed Oct. 10, 2014.
(Continued)

*Primary Examiner* — Maureen Wallenhorst
(74) *Attorney, Agent, or Firm* — Wegman, Hessler & Vanderburg (57) ABSTRACT

A method and system for measuring the adsorption potential of fly ash. A sample of the fly ash is mixed with an optically active reagent. The mixture is irradiated with light at a given wavelength and an optical parameter of the irradiated sample, such as intensity of optical absorbance or fluorescence emission is measured by an optical measuring apparatus. The adsorption capacity of the sample is determined as a function of the optical measurement. A controller is provided that communicates with the optical absorption measuring apparatus and controls flow of fly ash and sac-
(Continued)

rificial agent to a reaction zone or housing wherein the fly ash is contacted by the sacrificial agent.

21 Claims, 8 Drawing Sheets

(51) Int. Cl.
*C04B 28/02* (2006.01)
*C04B 18/08* (2006.01)
*C04B 40/00* (2006.01)

(52) U.S. Cl.
CPC .. *C04B 40/0039* (2013.01); *G01N 2021/7786* (2013.01); *Y02W 30/92* (2015.05)

(58) Field of Classification Search
CPC C04B 24/02; C04B 24/32; G01N 2021/7786; G01N 21/77; Y02W 30/92
USPC ....... 436/43, 164, 165, 172, 178; 422/82.05, 422/82.08, 82.09, 67
See application file for complete search history.

(56) References Cited

U.S. PATENT DOCUMENTS

| | | | |
|---|---|---|---|
| 6,706,111 | B1 | 3/2004 | Young |
| 7,892,349 | B2 | 2/2011 | Hill et al. |
| 7,942,566 | B1 | 5/2011 | Irvine |
| 8,440,015 | B1* | 5/2013 | LaCount ................. C04B 20/04 106/705 |
| 2004/0144287 | A1* | 7/2004 | Tardif ..................... C04B 18/08 106/705 |
| 2009/0199742 | A1 | 8/2009 | Hill et al. |
| 2010/0282595 | A1* | 11/2010 | Whellock ............... C04B 18/08 204/157.4 |
| 2012/0085264 | A1 | 4/2012 | Zhang et al. |
| 2012/0304893 | A1* | 12/2012 | Georges ................. C04B 28/02 106/677 |

OTHER PUBLICATIONS

International Preliminary Report on Patentability mailed Apr. 21, 2016 for PCT/US214/060001 filed Oct. 10, 2014.

* cited by examiner

METHOD AND DEVICE TO DETERMINE ADSORPTION CAPACITY FOR AIR ENTRAINING AGENTS

CROSS-REFERENCE TO RELATED APPLICATION

This application claims the priority benefit of U.S. Provisional Patent Application Ser. No. 61/889,749 filed Oct. 11, 2013.

FIELD OF INVENTION

This invention pertains to methods and systems that use the optical characteristics of chemical reagent adsorbate to determine the affinity of ash containing activated or unburned carbon to adsorb air-entraining agents (AEA). Activated carbon or a high level of unburned carbon in fly ash adversely affects fly ash use in concrete by interfering with the air-entraining agent's ability to entrain air in concrete.

BACKGROUND OF THE INVENTION

Air-entraining agents entrain or retain air in the fresh concrete by promoting the formation of stable and dispersed microscopic air voids. Air-entraining agents contain surface-active agents which concentrate at the air/water interface and lower the surface tension so that air voids can form and stabilize more readily. Surface-active agents are molecules, which at one end have chemical groups that tend to dissolve in water (hydrophilic groups) and adhere to wetted particles of fly ash and cement. At the other end, the surface-active agents have chemical groups that are repelled by water (hydrophobic groups). AEA's surface-active molecules tend to align at the air/water interface with their hydrophilic groups in the water and the hydrophobic groups in air. The hydrophobic groups have the affinity to also adhere to activated carbon or unburned carbon introduced into the concrete by the fly ash. Hydrophobic groups that adsorb on carbon surfaces are not available to entrain air voids. The loss of an AEA's ability to entrain an adequate amount of air is detrimental to the durability of concrete.

The volume of air voids required to provide optimum freeze-thaw protection in concrete is practically maintained in the 4%-8% range or more desirably 5%-7% by volume of concrete. The presence of activated carbon, which adsorbs AEAs, from fly ash in concrete, causes less than an optimal air void content to be obtained in concrete; thus, resulting concrete is more susceptible to damage from frost formation in concrete pores.

To mitigate the impact of activated carbon, the ash can be treated with a sacrificial agent to passivate the carbon adsorption capacity and prevent it from adsorbing excessive amounts of AEAs when used in concrete. In order to determine the accurate dosage for addition of the sacrificial agent, the adsorption capacity of carbon containing fly ash must be accurately determined. The level of carbon in ash and its adsorption capacity vary depending on power plant operating conditions. Electric power unit generation load, coal ash content, activated carbon injection rate, activated carbon surface area, operating conditions of burner, boiler, and air pollution control systems, etc., result in varying levels of carbon and variability in ash adsorption capacity. In order to determine the appropriate dosage of the sacrificial agent, the ash adsorption capacity must be periodically determined. The manual foam index test is typically used to determine the fly ash affinity to adsorb AEAs. The foam index test is subjective and cannot be automated. Methylene blue or acid blue adsorption can be used to determine the adsorption capacity of fly ash. These manual test procedures have been used in the lab and for field testing to periodically determine ash adsorption capacity.

SUMMARY OF THE INVENTION

To provide continuous monitoring of the variable adsorption capacity, a novel method and automated device are disclosed herein. The continuous monitoring of carbon in ash activity level can be used to assure ash quality for sale into concrete markets. This novel method can also provide real time adsorption capacity measurements for quality control in conjunction with an ash treatment system by determining the accurate dosage of the sacrificial agent needed to passivate the carbon in ash. An ash treatment system used in conjunction with this ash quality monitoring device can provide for synchronized addition of the sacrificial agent to the ash. To further improve the effectiveness of ash mitigation, the mechanical system used to transfer the ash from the silo into the truck or rail tanker can be improved by providing flow control and accurate measurement of the ash mass flow rate. The ability to control and measure ash mass flow rate coupled with the novel method of diagnosing the quality of the ash provides an ideal system to accurately passivate the carbon in ash. A further improvement to the passivation process involves diluting the sacrificial agent with an inert solvent to broaden the liquid application rate, provide a tamer dose response, and allow more thorough contact with ash.

In summary, the novel improvements to carbon passivation herein disclosed include the following:
  a diagnostic test that captures the chemisorption capacity of activated carbon/ash using optical characteristics of the reagent adsorbate;
  a reformulated sacrificial reagent to provide a tamed dose-response function and allow for better distribution throughout the ash; and
  an improved ash handling and reagent injection system to provide uniform and accurate distribution of reagent in ash.

The basic components of the photometric based diagnostic test and the automated sensor/device are:
  1. Sample Extraction—The device extracts a representative sample from the ash handling system at the coal fired plant, ash storage terminal, or concrete producer storage silo. The extraction can be done pneumatically, by gravity, or by means of screw auger. The samples can be extracted from ash transfer lines, electrostatic precipitator hopper, silo, bins, and any other mechanical systems carrying, storing, or transporting fly ash. The sample extraction component will deliver the extracted ash sample to the testing unit which can be located at a different location.
  2. Sample Weighting—A sample weighting component is used to determine the weight of the ash sample used in the analysis. The sample weighting component may consist of a weight chamber with load cells or a constant volume chamber where the weight is determined by calculation using the unit weight of the ash.
  3. Ash Slurry Reaction Chamber—A known water volume is added to the predetermined amount of ash sample to form an ash/water slurry. The slurry is stirred, and a known amount of optically active test reagent is added to the slurry. The reagent is allowed to adsorb on the ash and its carbon content.

4. Adsorbate Water Extraction—Water containing the non-adsorbed fraction of the adsorbate reagent is extracted from the ash slurry. Ash solids are filtered out to obtain a solids-free aqueous filtrate. The aqueous filtrate is transferred to the measurement cell to determine the residual reagent concentration.

5. Photometric Sensor—In the photometric sensor, the water containing residual reagent is irradiated with light at an optimal excitation wavelength. For example, many commercially available AEAs can be irradiated within the ultraviolet region of the electromagnetic spectrum. The excitation light interacts with the residual reagent molecules causing them to absorb and then emit or fluoresce at a different wavelength. The amount of fluorescence or absorbance measured by the sensor is directly proportional to the concentration of residual reagent in solution.

6. Central Processing Unit—The central processing unit contains the software needed to operate the sensor/device components and process the sensor response into reagent concentration, calculate the amount of reagent adsorbed on the ash, and export a signal to an indicator or controller which monitors and controls the ash treatment system.

In one exemplary embodiment, the above listed analytical steps may be performed manually or be fully automated to operate an ash treatment system to mitigate the impact of activated carbon in ash. The adsorption capacity determined by this novel method is used to calculate the amount of sacrificial agent needed to passivate the fly ash. Accordingly, the fly ash is sprayed with an accurate dosage of passivating reagent (i.e., sacrificial agent) to neutralize its impact on AEAs used in concrete mixes or concrete related products.

In another embodiment, a semi-automated process is achieved wherein an operator or the like would extract a sample and place it in the ash/slurry chamber. Then, the remaining process steps could be automated.

In certain exemplary embodiments, the components of the invention may be summarized as:

1. A novel ash activity sensor that can detect low levels of carbon in ash by measuring the adsorption capacity of the carbon/ash material. The sensor can be automated for real-time/on-line measurements. The sensor can be used for either quality assurance or quality control in conjunction with an ash treatment system.

2. A reformulated ash treatment reagent with a tamed dose-response function for handling carbon in ash variability.

3. An improved reagent injection system to provide accurate/uniform distribution of reagent in ash using real-time signals from the adsorption sensor and ash loading rate.

Item 2 may be viewed as an improvement on the original technology reported in U.S. Pat. No. 6,706,111, incorporated by reference herein. For example, the sacrificial agent or as stated in the '111 patent, the "treatment agent to control adsorption potential" can include an ethoxylate, such as nonylphenol ethoxylate surfactant (NPES), sodium lauryl sulfate or tall oil. In accordance with one aspect of the present invention, this sacrificial agent may be diluted with dissolved in ethanol, methanol, propylene glycol, water or any such inert diluent (inert re: carbon in ash) to tame it and minimize overdose potential. For example, in some preferred embodiments, propylene glycol acts as a solvent/dispersant to allow distribution of the NPES when sprayed on the fly ash and when the fly ash is incorporated into concrete. A small amount of defoamer may also be added.

Certain aspects of the invention are directed toward a method of measuring the adsorption capacity of fly ash. A fly ash sample is obtained, and an UV-VIS-NIR or IR optically active reagent is added to the fly ash sample to result in an optically active sample. The optically active sample is irradiated with light at a given wavelength. An optical parameter of the irradiated sample is measured, and the adsorption capacity of the fly ash is determined based upon the measurement of the optical parameter. In certain exemplary embodiments, the method is automated and provided in real time.

Additionally, in other embodiments, the measurement of an optical parameter of the irradiated sample comprises measuring the intensity of fluorescence emission of the optically active sample and the adsorption capacity is determined by correlating the intensity of the fluorescence emission of the optically active sample with the fluorescence emission intensity of a known amount of the optically active reagent. In some cases, the optically active reagent may be a chromophore or fluorophore or the optically active reagent may comprise an air entraining agent.

In certain exemplary embodiments, water may be added to the fly ash sample or to the optically active sample with an aliquot of liquid being drawn from the optically active sample and irradiated.

In accordance with certain aspects of the invention, a sacrificial agent is added to the fly ash after the adsorption capacity of the fly ash has been determined. This addition may be made in an automatic, real-time fashion.

In other exemplary embodiments, information pertaining to the adsorption capacity of the fly ash is inputted to a controller, and in response to a signal sent by the controller, a sacrificial agent or the like is added to the fly ash. In some embodiments, the chemical agent may be chosen from the group of sacrificial agents and air entraining agents and mixtures thereof. The chemical agent may be an air entraining agent itself, and in some instances, the chemical agent is an ethoxylated nonylphenol. The chemical agent may be combined with a diluent, and this diluent may, for example, be chosen from ethanol, methanol, propylene glycol, water, or any other inert diluent. The entire method may be performed in an automated, real time system. In other embodiments, the optically active reagent does not include methylene blue.

Further, in accordance with the invention, a system is provided for contacting fly ash from a fly ash supply source with a sacrificial agent from a sacrificial agent supply source. The system comprises a fly ash flow control device that is operatively associated with the fly ash supply source. Additionally, a sacrificial chemical agent flow control device is operatively associated with the sacrificial agent supply source. An optical parameter measuring apparatus is provided for measuring the optical absorbance or fluorescence emission from a fly ash sample. A controller in communication with the optical parameter measuring apparatus is provided, and this controller is configured to receive input from the optical parameter measuring apparatus and determine the adsorption capacity of the fly ash sample as a function of that input. A reaction zone may be provided for receiving the fly ash from the fly ash supply source, and the sacrificial agent to treat the fly ash by contact of the sacrificial chemical agent with the fly ash. The controller is configured to communicate with the fly ash flow control device and the sacrificial chemical agent flow control device to regulate the flow of same to the reaction zone.

In other embodiments, the system comprises an air source in communication with the sacrificial agent in the reaction zone to atomize the sacrificial agent as it contacts the fly ash. In other embodiments, an atomization nozzle is provided in operative association with the sacrificial agent and the air source in the reaction zone. A conveying device, such as a gravity chute or the like, is configured to transfer fly ash from the reaction zone to a transport carrier or stock pile. In still other embodiments, the optical parameter measuring apparatus is configured to measure fluorescence emission of the optically active reagent in contact with the fly ash sample.

Exemplary embodiments of the invention are illustrated in the appended drawings.

DETAILED DESCRIPTION

As to the novel ash activity method, this pertains to a new analytical method that is more reliable and much more representative than Foam Index (FI) and Methylene Blue (MB) testing. In one exemplary embodiment, it uses actual air entraining agents (AEAs) of interest to the particular market and determines the amount of AEA adsorbed on carbon/ash in a slurry by measuring the residual AEA in water. Unlike Foam Index, this fluorescence based method can be automated. And unlike methylene blue, which is a surrogate sorbent, the fluorescent based method's sorbents (analytical reagent) may be the AEAs of specific interest to the ash and local concrete market. In one aspect of the invention, the optically active reagent applied to the fly ash excludes methylene blue and acid blue.

In one embodiment, the basic analytical steps (quantities could vary depending on scale) are:
Weigh a small amount of ash (40 to 80 grams)
Add a measured amount of water (200 ml)
Add incremental amounts of AEA to the ash/water slurry
Disperse the AEA in the ash slurry
Extract liquid from slurry
Measure fluorescence (which is proportional to AEA concentration in water)
Determine the amount of AEA remaining in solution
Calculate the amount of AEA adsorbed on ash It has been determined that the most commonly used AEAs do indeed fluoresce, and they emit light in the range 350-480 nm when excited with light in the range 300-330 nm. Exemplary AEAs include: Grace Daravair 1000, BASF Micro Air, Sika Air, BASF AE-90, Euclid Eucon 40, Grace Darex AEA, and MBVR. These are classified chemically as

| AEA | Chemical Identity |
|---|---|
| Grace Daravair 1000 | Aqueous solution of neutralized resin acids and rosin acids |
| BASF Micro Air | Tall oil, fatty acids, polyethylene glycol |
| Sika Air | Tall oil fatty acids, fatty acids, castor oil, sodium hydroxide, diethylene glycol |
| BASF AE-90 | Rosin |
| Grace Darex AEA | Fatty Acids, tall oil, potassium salts, sodium dodecylbenzene-sulfonate, potassium hydroxide |
| Euclid Eucon Air 40 | Water, tall oil, sodium salt, 2-butoxy ethanol, glutaraldehyde |

Exemplary fluorescent excitation, emission, and counts an arbitrary unit describing the intensity of light detected at the central wavelength for these materials is as follows:

| AEA Sample | Excitation Wavelength (nm) | Emission Peak Central Wavelength (nm) | Emission Peak Range (nm) | Intensity at CWL (Arbitrary Units) |
|---|---|---|---|---|
| Grace Daravair 1000 | 280 | 390 | 340-470 | 800 |
| | 300 | 390 | 340-470 | 2000 |
| | 330 | 400 | 370-470 | 6600 |
| | 350 | 410 | 370-470 | 9000 |
| | 370 | 410 | 380-480 | 8500 |
| | 400 | 480 | 430-530 | 2400 |
| BASF Micro Air | 280 | 380 | 350-440 | 6000 |
| | 300 | 380 | 350-440 | 8500 |
| | 330 | 380 | 350-450 | 9600 |
| | 350 | 410 | 370-470 | 2500 |
| | 370 | 440 | 390-490 | 1600 |
| | 400 | 480 | 430-530 | 1000 |
| Sika Air | 280 | 380 | 330-450 | 1200 |
| | 300 | 380 | 350-450 | 2200 |
| | 330 | 410 | 360-460 | 4600 |
| | 350 | 420 | 390-470 | 6000 |
| | 370 | 440 | 390-510 | 6600 |
| | 400 | 490 | 440-540 | 4400 |
| BASF AE-90 | 280 | 380 | 340-440 | 3700 |
| | 300 | 380 | 340-440 | 6400 |
| | 330 | 390 | 350-470 | 8500 |
| | 350 | 410 | 370-510 | 7400 |
| | 370 | 450 | 390-530 | 6800 |
| | 400 | 480 | 430-530 | 5200 |
| Euclin Eucon 40 | 280 | 380 | 360-430 | 3500 |
| | 300 | 380 | 350-450 | 6800 |
| | 330 | 390 | 350-450 | 8000 |
| | 350 | 410 | 380-470 | 5200 |
| | 370 | 420 | 390-490 | 4700 |
| | 400 | 480 | 430-530 | 2300 |

-continued

| AEA Sample | Excitation Wavelength (nm) | Emission Peak Central Wavelength (nm) | Emission Peak Range (nm) | Intensity at CWL (Arbitrary Units) |
|---|---|---|---|---|
| Grace | 280 | 310-360 | 290-410 | 4800 |
| Darex AEA | 300 | 380 | 330-450 | 6200 |
| | 330 | 390 | 330-450 | 2200 |
| | 350 | 420 | 380-460 | 2500 |
| | 370 | 440 | 440-490 | 1600 |
| | 400 | 480 | 430-530 | 900 |

In some embodiments, the optically active reagent to be added to the fly ash is a fluorophore such as quinine, or as per the above can be the AEA itself. By "optically active", the agent must be shown to absorb light at a given wavelength or be capable of fluorescing at a distinctly different wavelength. In fluorescence, the reagent emits light at a different wavelength from the irradiation or excitation wavelength. The amount of optically active reagent is determined by the absorbance measurement or the intensity of the emitted wavelength. In certain embodiments, the optically active reagent comprises a conjugated dienyl molecule.

Optical parameters then such as absorbance intensity or emitted wavelength intensity (fluorescence intensity) are compared, for instance, with calibration standards of known reagent concentrations in order to determine the amount of reagent present in a give fly ash sample.

Accordingly, it is apparent that in certain embodiments, a method and system are provided that measures the adsorption capacity of fly ash. First, a fly ash sample is obtained, and then an optically active reagent is added to the fly ash sample to produce an optically active sample. The optically active sample is irradiated with light at a given wavelength. Preferably, the light is irradiated at a monochromatic wavelength. An optical parameter of the irradiated sample is then measured, and as a result of this measurement, the adsorption capacity of the fly ash is determined. The overall method and system are provided in an automated, real time period.

In other embodiments, the step of measuring an optical parameter of the irradiated sample comprises measuring the intensity of fluorescence emission of the optically active sample, and the adsorption capacity of the fly ash is determined by correlating the intensity of the fluorescence emission with the fluorescence emission of a known concentration of the reagent. In some instances, the optically active reagent may be a chromophore or fluorophore such as quinine sulfate. In other cases, the optically active reagent may be an air entraining agent or a surrogate surfactant such as the ethoxylated alkyl phenols.

In further embodiments, water may be added to the fly ash sample or to the optically active sample. Then, an aliquot of liquid drawn from the optically active sample for irradiation and subsequent optical intensity measurement.

In certain embodiments, as a result of the determination of the adsorption capacity of the fly ash, a sacrificial agent is added to the fly ash. This addition of sacrificial agent can also be accomplished in an automated, real time period. As to the sacrificial agents that can be added, a host of these is disclosed in U.S. Pat. No. 7,892,349, the entire disclosure of which is incorporated by reference. Exemplary sacrificial agents include aromatic carboxylic acids and salts thereof, hydroxy substituted aromatic carboxylic acids or their salts, polyethylene glycol, alcohols, glycol ethers, polyglycols, aromatic sulfonates, esters, alcoholamines, alkyl carboxylates, aromatic compounds bearing sulfonate groups, carboxylate groups, amino groups or combinations of such groups, and low molecular weight glycols and glycol derivatives (i.e., those having molecular weight of 2000 Da or less, preferably 1500 Da or less), and combinations of such compounds. By testing a variety of compounds as potential sacrificial agents, it has been discovered that the following compounds, in particular, are effective as sacrificial agents to varying degrees: benzylamine, sodium 1-naphthoate, sodium 2-naphthalene sulfonate, sodium di-isopropyl naphthalene sulfonate, sodium cumene sulfonate, sodium di-butyl naphthalene sulfonate, ethylene glycol phenyl ether, ethylene glycol methyl ether, butoxyethanol, di-ethylene glycol butyl ether, di-propylene glycol methyl ether, polyethylene glycol and 1-phenyl 2-propylene glycol. All of these compounds, and others mentioned later in this description, are known and commercially available from suppliers of organic chemical (e.g., from Aldrich, Rutgers, Stepan, Anachemia, Baker, BDH, Eastman, Fisher, Mallinckodt, Polysciences, Pfalz & Bauer, TCI, etc., all of which are well know suppliers of chemicals to persons in this field of art). They are preferably used in pure or substantially pure form.

In still further embodiments, a controller is provided in cooperative association with the measurement apparatus by which the optical parameter of the irradiated sample is made. The controller receives input from the optical measurement device and sends a signal to a flow control or similar device to feed the sacrificial agent to the fly ash. In further embodiments, as a result of the determination of the adsorption capacity of the fly ash, an air entraining agent is added to the fly ash. In some cases, the chemical agent, namely the sacrificial agent, air entraining agent, or combination thereof, is combined with a diluent. In this manner, the dose response curve of the chemical agent addition can be "flattened" (i.e., decreased slope) within the relevant addition range so as to minimize deleterious effects that may otherwise be caused by over dosage. In certain preferred embodiments, the diluent is ethanol, methanol, propylene glycol, water, or any such inert diluent.

The invention will be further described by the following Examples which are illustrative of certain embodiments of the invention and should not be viewed as limiting the invention.

EXAMPLES

In some of the following examples, a "burn out series" was prepared from fly ash. A "burn out series" is a set of ash samples that are identical except that they contain incrementally increasing percentages of carbon. This was accomplished by heating a portion of a fly ash sample to 650° C. in an oven for eight hours to ignite residual carbon and produce a fly ash sample which was essentially 'carbon-free' for use as a baseline material. This material was mixed with the original unburned sample which still contained the original amount of carbon to produce samples containing 25% to 85% burn out ash with the remaining portion of ash being the original sample. The result was a series of similar fly ash samples with differing amounts of carbon. These types of fly ash samples are referred to herein as a "burn out series".

Figure 1:
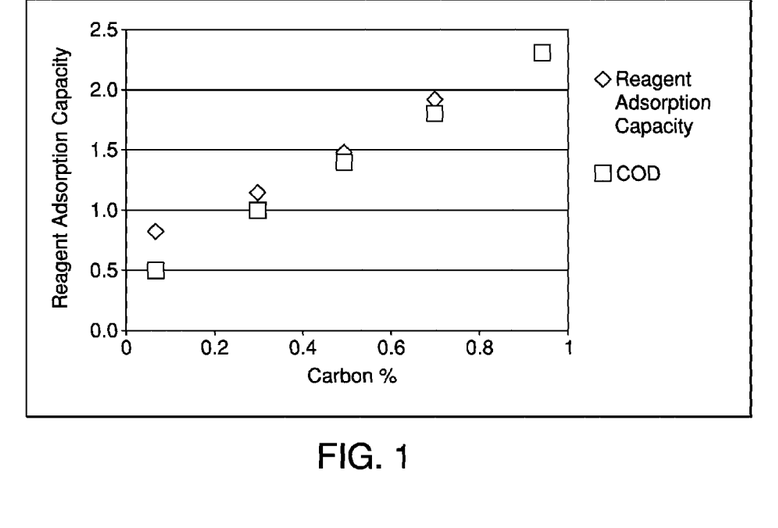
FIG. 1 is a graph correlating the COD methods and the fluorescent measurement method in determining the adsorption capacity of various fly ash samples.

Validation of Adsorption Testing:

Measuring concentration via fluorescence was validated by chemical oxygen demand (COD) testing of identical samples. COD is an accepted laboratory method which measures the amount of oxygen required to fully oxidize organic compounds such as NPES and air entraining agents and can be used to determine the concentration of organic species in solution. FIG. 1 is a graph showing correspondence between the COD method and fluorescence method of the invention in making measurement of the adsorption capacity of fly ash samples.

Example 1

In this example, ash samples from a burn out series were tested to determine the RestoreAir 2.2 (RA 2.2) dosage via Foam Index (FI) testing and the fluorescence method for comparison. (RA 2.2 is an aqueous solution of NPES propylene glycol and other minor constituents).

Foam Index:

The Foam Index (FI) test is a historically accepted and frequently utilized test method for determining the appropriate AEA dosage in concrete mixes. Fly ash can be accepted or rejected based upon the FI value, and the acceptable value is based upon the intended use and particular market. Various FI methods have been developed; however, they follow the same basic steps. A fly ash sample is weighed (40 grams for class C and 80 grams for class F) and mixed with 200 mL of deionized water. After the initial mixing, an AEA is added dropwise to the sample and mixed again. The sample is then observed to determine if stable foam has been achieved. A sample has exhibited stable foam when a uniform layer of bubbles has covered the entire surface of the sample, and the bubbles on the surface have stopped popping for at least 10 seconds. If the sample has not achieved stable foam, additional AEA is added, and the sample is mixed and observed again. This is continued until stable foam is formed. Once the foam is stable, no AEA is added to the sample, and it is mixed one more time. The sample is again observed, and if stable foam remains, the number of drops added is recorded as the FI value. If the foam has dissipated after the second mixing, additional AEA is added, and the cycle continues.

In this particular example, a fly ash with a FI value of 10 drops was considered acceptable by the market. Various burn out series ash samples were prepared to obtain fly ash samples with different carbon contents. Different carbon contents allowed the samples to have various initial FI values which ranged from 10 drops to 98 drops of AEA. RA 2.2 was added to samples from the burn out series to obtain an acceptable FI value of 10 drops of AEA. The initial FI was plotted against the RA 2.2 dosage to obtain a direct relationship between RA 2.2 dosage and initial FI values.

One Point Isotherm via Fluorescence:

The concentration of solutions containing fluorescent molecules, such as air entraining agents and NPES, can be determined by measuring the fluorescence intensity of the solutions. In this example, NPES was mixed with carbon containing ash samples to determine the amount of NPES adsorbed by the samples. A burn out series was prepared from class C ash. One particular sample of the burn out series was prepared which had an acceptable FI value of 10 drops of AEA, herein referred to as the "acceptable sample." This sample was used to determine the excess amount of NPES adsorbed onto a typical ash sample containing higher carbon contents than the acceptable sample.

A 40 gram fly ash sample of each of the burn out series ashes was weighed, and each sample was individually mixed with 200 mL of 700 mg/L NPES solution for 15 minutes and vacuum filtered using a number 4 Whatman filter. The filtered ash cake was then washed four times with 50 mL aliquots of DI water for a total of 200 mL of wash water. The resultant filtrate was gently mixed by hand, and its volume was recorded. Subsequently, the filtrate was tested to determine the fluorescence intensity which indicated the residual NPES concentration. The adsorbed NPES was calculated by determining the difference in the concentration of NPES for the initial solution and the resultant filtrate.

The value of NPES adsorbed by the acceptable sample (FI value of 10 drops of AEA) was subtracted from each of the adsorption values of the remaining burn out series samples. The calculated difference indicates the excess amount of NPES adsorbed by each sample. This value was then converted from milligrams of NPES adsorbed per gram of ash to RA 2.2 dosage in pounds of RA 2.2 per ton of ash.

Figure 2:
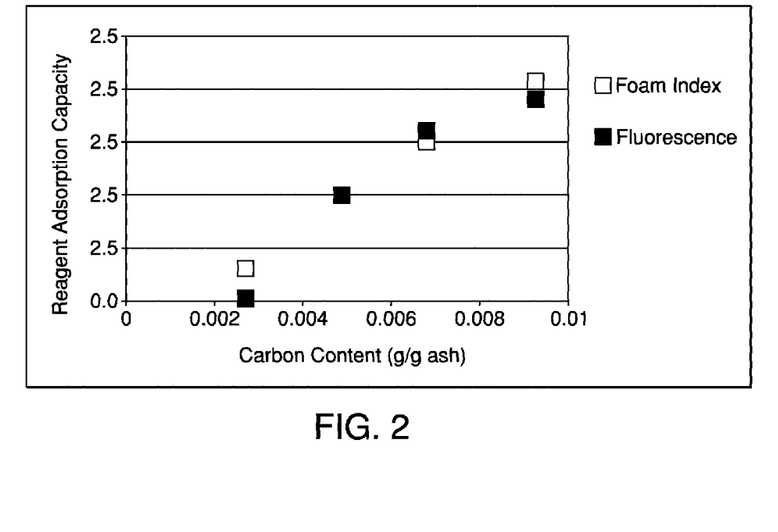
FIG. 2 is a graph comparing the amount of sacrificial agent dosage needed to treat various fly ash samples as determined by both the fluorescence method of the invention and the conventional foam index (FI) method.

Comparison of RA 2.2 Dosages Determined by FI and Fluorescence:

FIG. 2 shows the comparison of the calculated RA 2.2 dosages using the FI method and the fluorescence method. The two curves overlap indicating similar abilities to predict RA 2.2 dosages (FIG. 2).

Example 2

Carbon in fly ash, whether native or activated, has an adsorptive quality which increases AEA demand for ready mix concrete producers who need to entrain sufficient air voids in concrete for protection against freeze/thaw cycles. The amount by which the AEA is increased depends on many factors, in particular, the amount of carbon present, type of carbon, and its adsorption capacity. Currently, determination of the end point of a FI test is the most readily available and utilized test in practice for this purpose. The end point of a FI test indicates the point at which the adsorption capacity of carbon has been met by the AEA and just slightly exceeded. The excess in solution is evident upon formation of stable foam on the surface of the slurry.

Foam Index Volume Determination:

In this example, fluorescence intensity was measured to determine the point at which sufficient NPES was available in solution to meet the adsorption capacity demands of carbon present and slightly exceed that point (i.e., the breakthrough point). The slight excess was evident by an increase in fluorescence intensity. It was hypothesized that this point would correlate to the NPES FI point, so a FI test was conducted on each of five samples of a burn out series. In order to obtain a more accurate dosage of NPES, the exact volume of NPES added (herein referred to as the FI volume), rather than a dropwise measurement, was used. The FI volume was used to determine a starting point for fluorescence testing.

Figure 3:
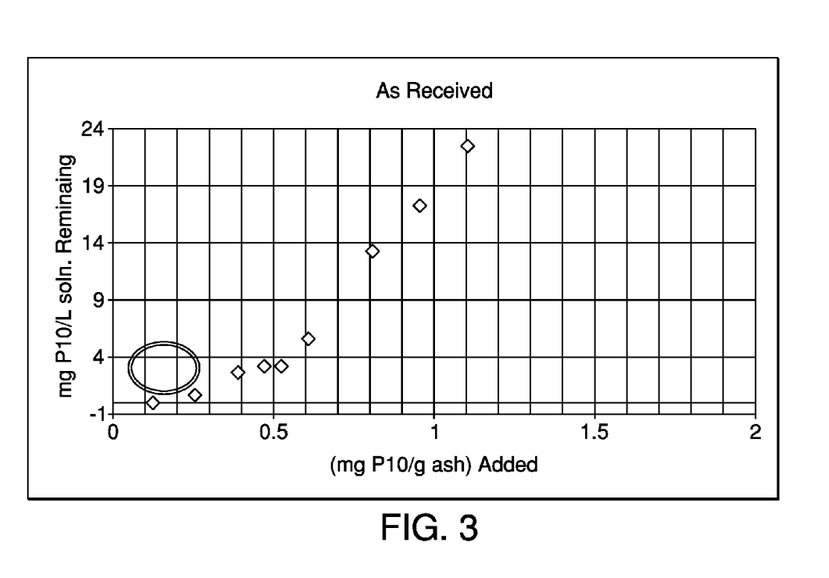
FIGS. 3-7 are graphs showing the breakthrough amounts of NPES determined by fluorescent methods for various burn out fly ash samples as dispersed in Example 2.
Figure 4:
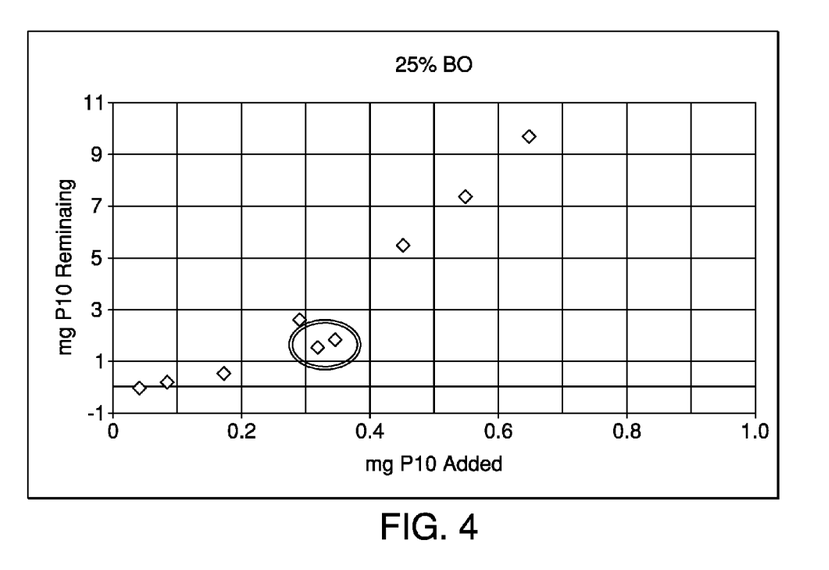
Figure 5:
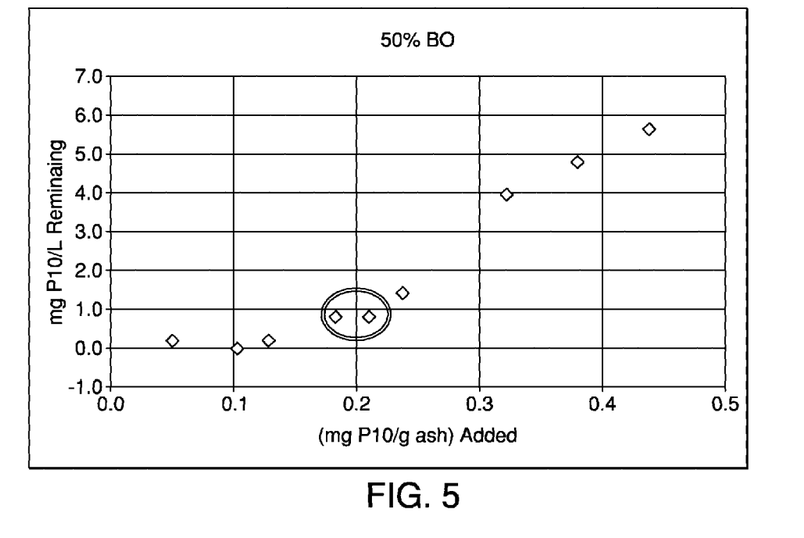
Figure 6:
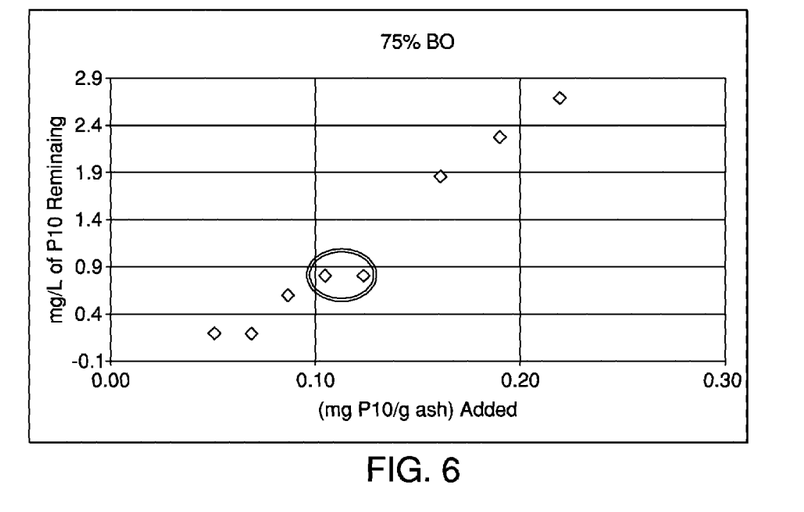
Figure 7:
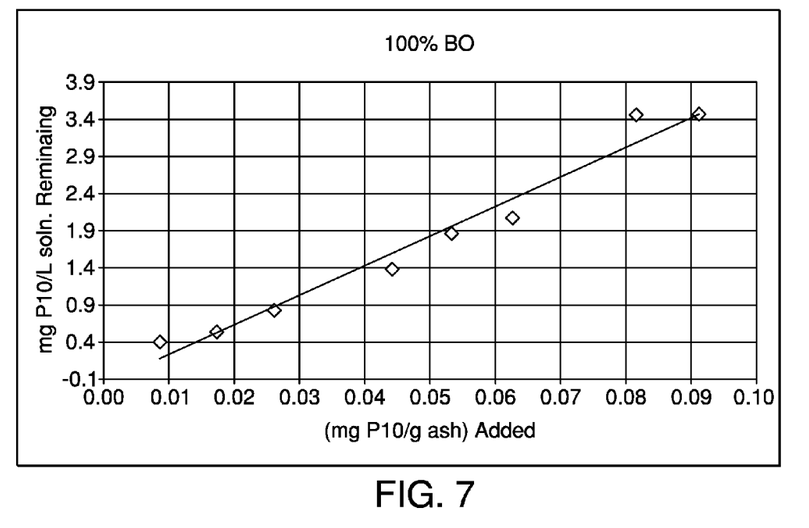

Fluorescence Testing:

A 120 g sample of class C fly ash was continuously mixed with 600 mL of DI water using a magnetic stir plate. A 1% NPES solution was added in 9 aliquots which corresponded to three points prior to the FI volume, three points near the FI volume, and three points which exceeded the FI volume. After each addition, a 10 mL sample was withdrawn using a 10 mL slip tip syringe while the slurry was mixing. The sample was subsequently vacuum filtered, and the ash cake was washed with 50 mL of DI water to ensure all available NPES was collected in the filtrate. The volume of the filtrate was measured, and the sample was set aside for fluorescence testing. This was continued until all nine additions of 1% NPES were added, and the filtrate had been collected. Fluorescence testing was conducted to determine the NPES concentration present in each of the nine filtrate samples. This procedure was repeated for each of the five fly ash samples from the burn out series. FIGS. 3-7 are graphs showing the breakthrough amounts of NPES as determined by fluorescence methods for the various burn out samples that were tested. FIG. 3 shows the breakthrough test results for a fly ash sample as received, with FIGS. 4-7 showing such results for varying degree burn out (80) samples as designated in each figure. The amount of NPES added was plotted against the amount of NPES remaining in solution, and the FI volume was determined to correlate to the leveling off of the curves just prior to the linear increase in concentration in all samples except the 100% BO (burn out) sample. This is to be expected, because the 100% BO sample has no carbon present to interfere with linear increases in NPES concentration. (Note: P10=NPES).

Figure 8:
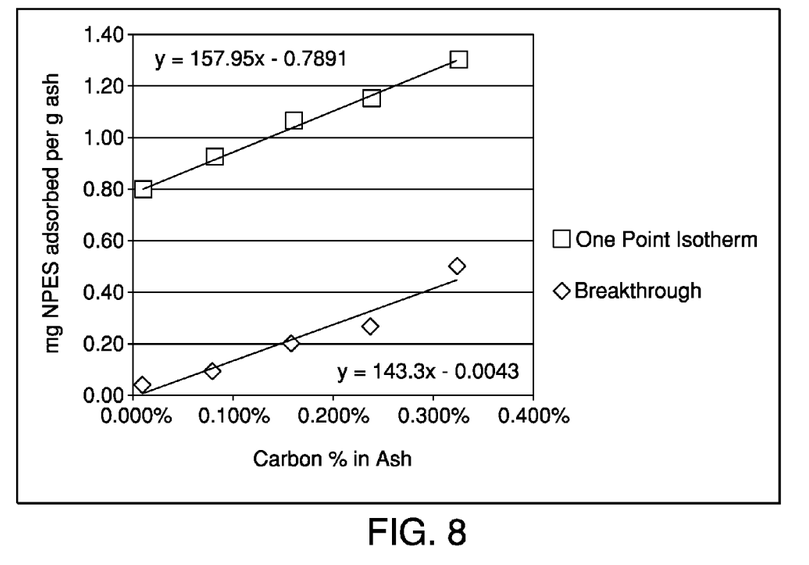
FIG. 8 is a graph comparing adsorption measurements using both the one point isotherm method and the breakthrough method.

The reagent adsorption capacity (mg of NPES adsorbed per g of ash present) was subsequently measured using One Point Isotherm testing as explained in Example 1 for each of the five samples from the burn out series. A comparison of the breakthrough test results and One Point Isotherm results indicated a linear relationship with similar slopes and a shift in the y-intercept (FIG. 8). This is to be expected as carbon adsorption exhibits a typical Langmuir Isotherm and is concentration driven. In One Point Isotherm testing, a 700 mg/L solution is used, while a much lower concentration is used in breakthrough testing.

Traditional Foam Index Testing:

Traditional Foam Index testing as described in Example 1 was conducted on the five samples from the burnout series using MicroAir in a 1:1 solution with DI water as the AEA.

Figure 9:
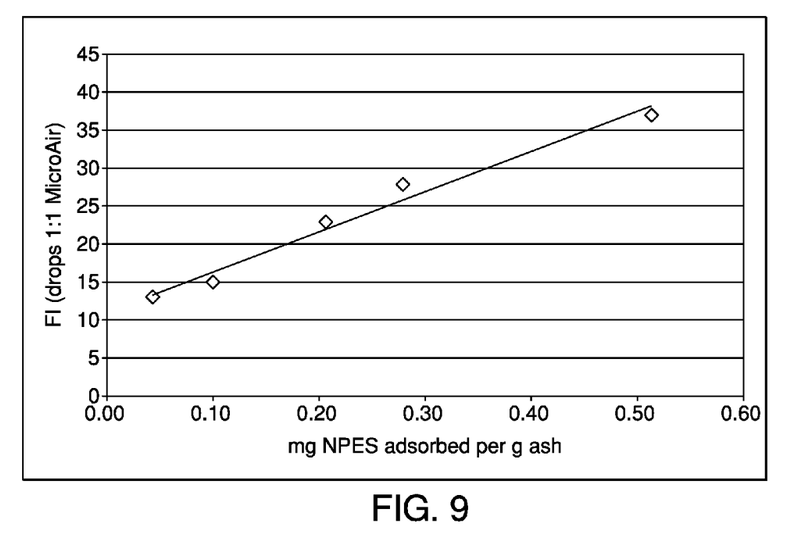
FIG. 9 is a graph showing breakthrough adsorption values plotted against traditional FI test results using 1:1 MicroAir as the AEA.

Plotting the adsorption values (mg NPES adsorbed per g of ash present) measured by the breakthrough method against FI values obtained from traditional FI testing using 1:1 MicroAir indicates a direct linear relationship between breakthrough adsorption and FI values (FIG. 9).

Example 3

Figure 10:
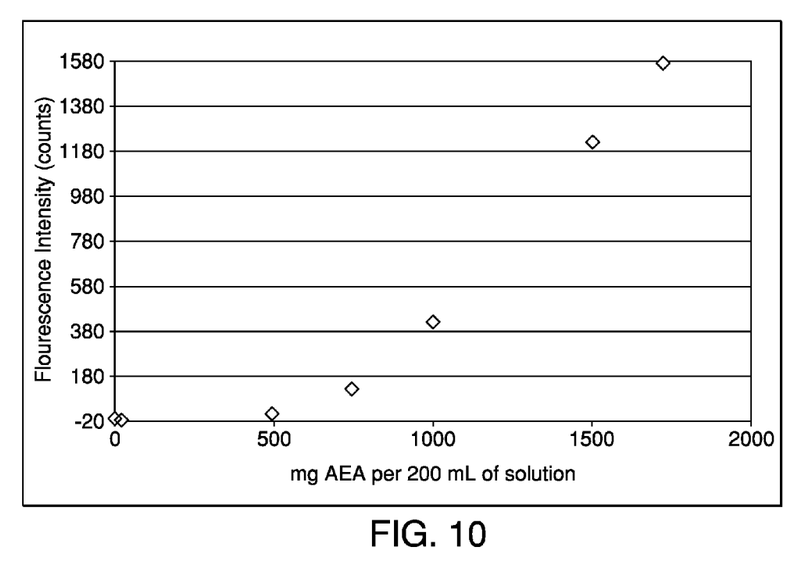
FIG. 10 is a graph showing fluorescence intensity measurements for increasing AEA concentrations as discussed in Example 3.

In this example, 280 mg of class F fly ash was mixed with 700 mL of an AEA solution for 60 minutes at 300 rpm with an automated paddle mixer. Each sample was allowed to set for 15 minutes after mixing to allow the ash to settle to the bottom of the beaker. Filtrate was drawn from the top of the beaker with a syringe and filtered using a 25 millimeter diameter 0.2 micrometer PTFE membrane filter with a polypropylene housing. The filtrate was subsequently tested via fluorescence to determine the effect of increasing the AEA dosage in identical class F fly ash samples. FIG. 10 plots the intensity of the fluorescence measurements versus AEA concentration.

Example 4

Figure 11:
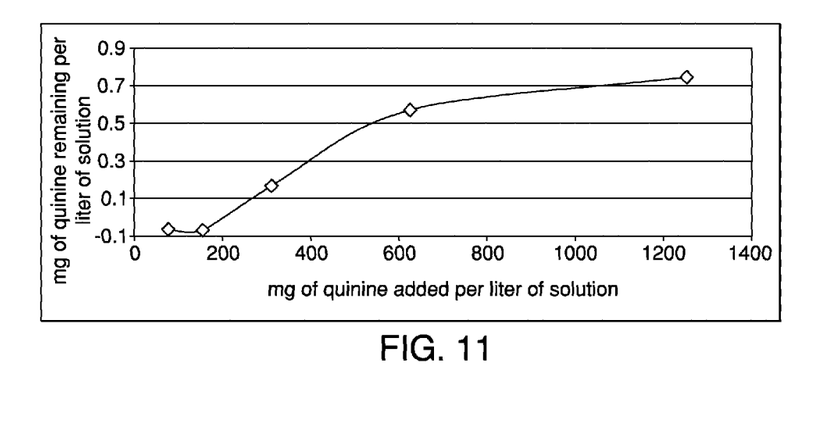
FIG. 11 is a graph showing amounts of quinine remaining with the ash per concentration of quinine solution originally mixed with the ash as explained in Example 4.

In this example, quinine was used as the adsorbing reagent. A 140 gram sample of class C ash with a carbon content of 0.8066% (by LECO) was mixed in a one-liter beaker for one hour at 300 rpm using an automated paddle mixer with 700 mL of quinine solution. After mixing, each ash slurry was allowed to set for 15 minutes. Filtrate was removed from the top of the beaker with a syringe and filtered using a 25 millimeter diameter 0.2 micrometer PTFE membrane filter with a polypropylene housing. The filtrate was then tested via fluorescence to determine the residual quinine concentration. FIG. 11 is a graph showing the results of this testing.

Figure 12:
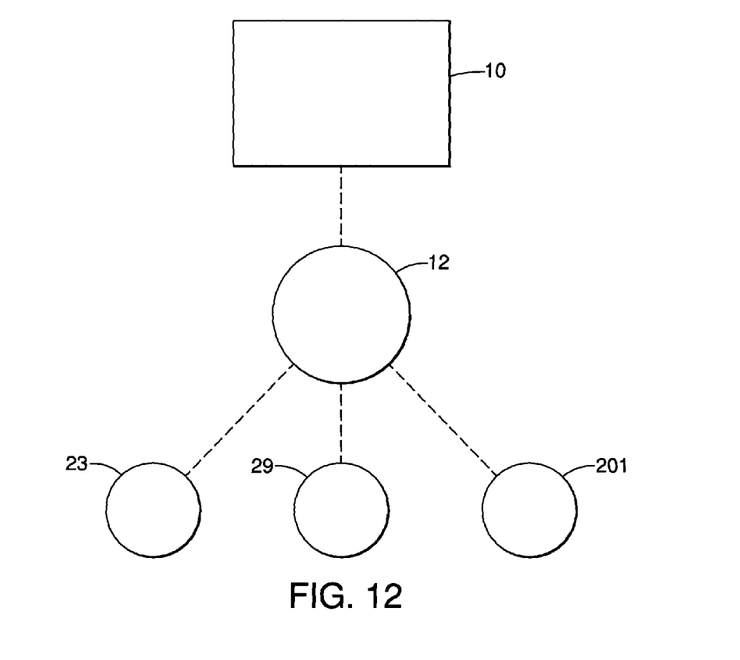
FIG. 12 is a schematic process control diagram showing continuous, real-time process controls that, in one embodiment, may be used to determine the adsorption capacity of fly ash samples and treat the fly ash with requisite amounts of sacrificial agent.
Figure 13:
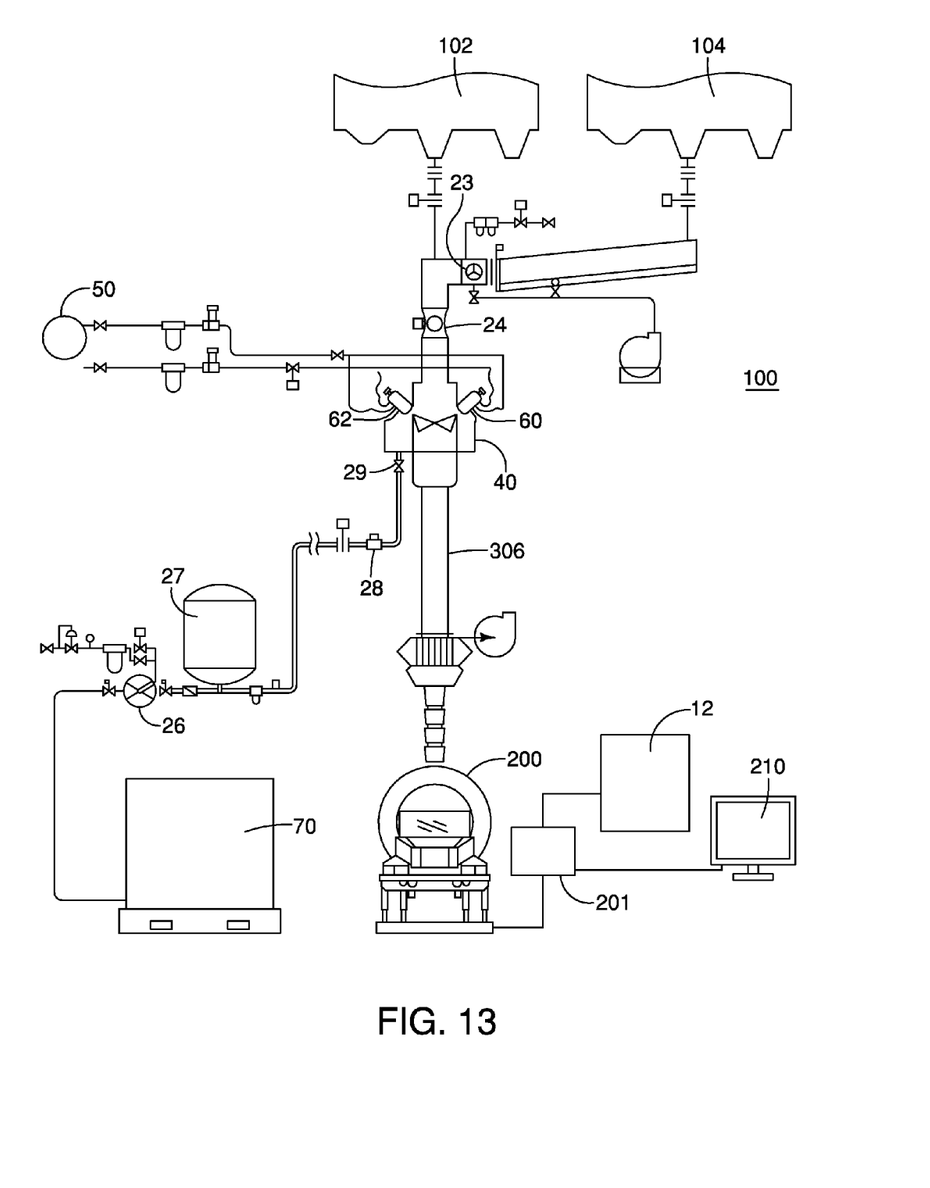
FIG. 13 is a schematic diagram showing one embodiment of a continuous fly ash adsorption capacity measurement and sacrificial agent treatment system that may be used in accordance with the invention.
Figure 14:
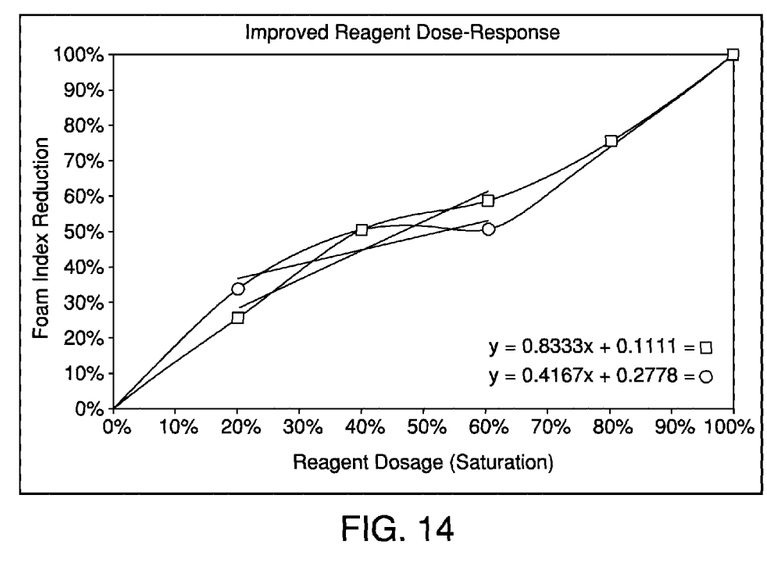
FIG. 14 is a graph showing reagent dosage versus foam index reduction for a NPES sacrificial agent treatment and a diluted NPES sacrificial agent treatment.

Turning now to FIGS. 12 and 13, a process schematic is shown illustrating continuous, real-time automated systems by which the adsorption capacity of a mass of fly ash can be accurately determined and subsequently treated with a sacrificial agent to control the adsorption potential of the fly ash. Turning first to FIG. 12, there is shown a control process diagram illustrating optical parameter measuring apparatus 10. Apparatus 10 can be any one of the known instruments in which measurements of optical absorption or fluorescence emission of a liquid sample can be made. Typically, these devices include a power supply connection source, a light source (preferably UV light source), a sample containing reservoir, and an absorbance or emission measuring analyzer capable of measuring the intensity of the absorbed light or emitted light of given frequencies. Exemplary apparatus 10 includes Photox by Cuom Sensors and Technology, Fenton, Mo.

Input from apparatus 10 is then conveyed to a controller 12 such as a programmable logic controller or computer. Calculations regarding the adsorption capacity of the fly ash sample are made therein as a function of the optical measurement of the fly ash sample/optically active reagent slurry fed to the analyzer 10. As stated above, the intensity count of the absorbance or fluorescence emission is related to the adsorbance capacity of the ash. The amount of sacrificial agent to be used to satiate this particular saturation level is calculated in terms of wt/wt (i.e., weight of saturation chemical needed to saturate the ash/weight of ash such as in pounds or tons).

Actuation signals from controller 12 are sent to the fly ash control valve 23, sacrificial agent flow control mechanism 29 and optionally to a flow detection or weigh scale instrument 201 operatively associated with a truck, rail car, or the like adapted to transport treated ash to the customer, to a stockpile, or to other storage area. Flow rates of the fly ash and sacrificial agent are thus monitored and controlled.

In one embodiment of the invention, an automated fly ash/sacrificial agent feed and treatment system can be provided. As shown in FIG. 13, the system 100 comprises fly ash supply tanks 102, 104 feeding fly ash to housing 40 at a controlled flow rate via the actuation signal received from flow control regulator 23. Shut off valve 24 is also provided in the fly ash feed system for additional flow control.

Fly ash is thus fed into housing where it is treated with a controlled amount of satiation agent flowing into the housing 40 through nozzles 60, 62. Compressed air from source 50 is fed into the housing nozzles 60, 62 to provide air required to atomize the satiation agent as it enters the housing to contact the fly ash flowing therein.

Satiation agent is fed from reservoir 70 via pump 26 and pressure regulation vessel 27 through the flow meter 28 into the nozzles under control of mechanism 29. A scale or flow meter 201 is operatively associated with truck 200, other transportation means, or stockpile. A conveyor 306 such as a gravity discharge chute allows for transfer of the treated fly ash to the transport device or stockpile. Input from device 201 is fed to controller 12 so that appropriate feedback and possible adjustment to actuation controls for fly ash control valve 23 and sacrificial agent flow control 29 may be made.

As stated above, it is sometimes desirable to add a diluent to the sacrificial agent in order to reduce the risk of overdosage of the sacrificial agent. In these cases, a solvent or liquid carrier that is inert to the carbon in the ash is mixed with the sacrificial agent. As a result of this dilution, the X, Y plot of reagent dosage (X=saturation Y=Foam Index Reduction) results in a lowered slope; increasing dosage accuracy. This can be seen in FIG. 14 wherein a NPES sample is compared to a NPES sample mixed with diluent. The diluted sample is shown by circles with the non-diluted samples denoted by squares. Here, the slope of the dose-response in the treatment range (20%-60% of saturation) is reduced by about half using the diluted reagent. Lowering the dose response slope will reduce the risk of overdosing.

Figure 15:
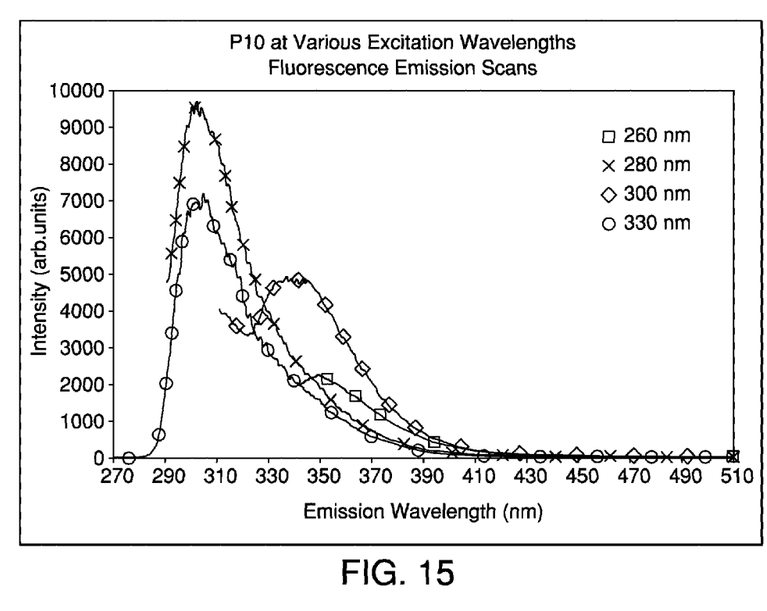
FIG. 15 is a graph plotting P-10 (NPES) emission intensity at various fluorescent excitation wavelengths.

FIG. 15 shows exemplary fluorescent emissivity intensities at a variety of excitation wavelengths for NPES.

In exemplary solutions of the sacrificial agent, the sacrificial agent (SA) may be present in aqueous solution in a weight amount of about 2-1:1 wt % (SA:diluent). In one preferred embodiment, NPES (SA) is present in a ratio of about 1.5:1 (SA:diluent). The diluent may be an alcohol or glycol, such as ethylene glycol or propylene glycol. At present, it is preferred to dilute the NPES with propylene glycol in an aqueous solution.

This invention has been described in conjunction with various exemplary embodiments. Various modifications of the disclosed embodiments and alternative embodiments will become apparent to those skilled in the art. The appended claims are intended to cover all such exemplary embodiments, modifications, and alternative embodiments.

The invention claimed is:

1. Method of measuring the adsorption capacity of fly ash comprising the steps of:
   a) obtaining a fly ash sample;
   b) adding an optically active reagent to the fly ash sample to produce an optically active sample;
   c) irradiating the optically active sample with light at a given wavelength;
   d) measuring an optical parameter of the irradiated sample; and
   e) determining said adsorption capacity based upon the measurement of the optical parameter, wherein the steps a) through e) are automated and provided in real time wherein said optical parameter is intensity of fluorescence emission of said optically active sample and step d) comprises measuring the intensity of fluorescence emission of said optically active sample and correlating said measured intensity of fluorescence emission of said optically active sample with a fluorescence emission intensity of a known amount of said reagent.

2. Method as recited in claim 1 wherein said optically active reagent is a chromophore or fluorophore.

3. Method as recited in claim 1 wherein said optically active reagent is an air entraining agent.

4. Method as recited in claim 1 wherein said optically active reagent is an adsorbate surfactant as a surrogate to air entraining agent.

5. Method as recited in claim 1 wherein water is added to said fly ash sample or to said optically active sample, and an aliquot of liquid is drawn from said optically active sample and irradiated.

6. Method as recited in claim 1 wherein after said step e) a sacrificial agent is added to said fly ash and wherein the addition of said sacrificial agent is accomplished in an automated fashion.

7. Method as recited in claim 1 wherein information pertaining to said adsorption capacity is inputted to a controller, and in response to a signal sent by said controller, a chemical agent is added to said fly ash.

8. Method as recited in claim 7 wherein said chemical agent is a member chosen from the group consisting of sacrificial agents, air entraining agents, and mixtures thereof.

9. Method as recited in claim 8 wherein said chemical agent is a sacrificial agent.

10. Method as recited in claim 8 wherein said sacrificial agent is preferentially adsorbed by said fly ash sample, compared to the adsorbance of an air entraining agent by said fly ash sample.

11. Method as recited in claim 8 wherein said chemical agent is an air entraining agent.

12. Method as recited in claim 8 wherein said chemical agent is ethoxylated nonyl phenol.

13. Method as recited in claim 8 wherein said chemical agent is combined with a diluent.

14. Method as recited in claim 13 wherein said diluent is ethanol, methanol, propylene glycol, water, or any such inert diluent.

15. Automated system performing the steps set forth in claim 1.

16. A method as recited in claim 1 wherein said optically active reagent does not include methylene blue or acid blue.

17. Method of measuring the adsorption capacity of a fly ash sample comprising the steps of:
   a) adding an optically active reagent to the fly ash sample to produce an optically active sample;
   b) irradiating the optically active sample with light at a given wavelength;
   c) measuring an optical parameter of the irradiated sample; and
   d) determining said adsorption capacity based upon the measurement of the optical parameter, wherein said optically active reagent does not include methylene blue or acid blue.

18. A system for contacting fly ash from a fly ash supply source with a sacrificial agent from a sacrificial agent supply source, said system comprising:
   a) a fly ash flow control device operatively associated with said fly ash supply source;
   b) a sacrificial chemical agent flow control device operatively associated with said sacrificial agent supply source;
   c) an optical parameter measuring apparatus for measuring optical absorbance or fluorescent emission from a fly ash sample;
   d) a controller in communication with said optical parameter measuring apparatus and configured to receive input from said optical parameter measuring apparatus and determine adsorption capacity of said fly ash sample as a function of said input;
   e) a reaction zone for receiving said fly ash from said fly ash supply source and said sacrificial agent from said sacrificial agent supply source to treat said fly ash by contact of said sacrificial chemical agent with said fly ash;
   said controller configured to communicate with said fly ash flow control device and said sacrificial chemical agent flow control device to regulate flow of said fly ash and said sacrificial chemical agent to said reaction zone, wherein said optical parameter measuring apparatus is configured to measure fluorescence emission of an optically active reagent in contact with said fly ash.

19. A system as recited in claim 18 further comprising a compressed air source in communication with said sacrificial agent in said reaction zone to atomize said sacrificial agent as it contacts said fly ash.

20. A system as recited in claim 19 further comprising an atomization nozzle in operative association with said sacrificial agent and said compressed air source in said reaction zone.

21. A system as recited in claim 18 further comprising a conveying device configured to transfer treated fly ash from said reaction zone to a transport carrier or a stockpile.

* * * * *